(12) United States Patent
Amisar

(10) Patent No.: US 8,124,420 B2
(45) Date of Patent: Feb. 28, 2012

(54) REAGENT, A KIT, AND A METHOD FOR DETECTING AND IDENTIFYING A WIDE RANGE OF ILLICIT DRUGS

(75) Inventor: Shai Amisar, Tel Aviv (IL)

(73) Assignee: Mistral Detection Ltd, Herzliya Pituach (IL)

( * ) Notice: Subject to any disclaimer, the term of this patent is extended or adjusted under 35 U.S.C. 154(b) by 61 days.

(21) Appl. No.: 12/674,733

(22) PCT Filed: Aug. 21, 2008

(86) PCT No.: PCT/IL2008/001149
§ 371 (c)(1),
(2), (4) Date: Feb. 23, 2010

(87) PCT Pub. No.: WO2009/027967
PCT Pub. Date: Mar. 5, 2009

(65) Prior Publication Data
US 2011/0117664 A1    May 19, 2011

Related U.S. Application Data

(60) Provisional application No. 60/935,762, filed on Aug. 30, 2007.

(51) Int. Cl.
*G01N 21/00*    (2006.01)

(52) U.S. Cl. ......... 436/164; 436/104; 436/166; 210/634
(58) Field of Classification Search .................... None
See application file for complete search history.

(56) References Cited

U.S. PATENT DOCUMENTS

4,771,005 A    9/1988    Spiro
6,787,366 B1    9/2004    Novak

*Primary Examiner* — Yelena G Gakh
*Assistant Examiner* — Robert Xu
(74) *Attorney, Agent, or Firm* — Frank H. Foster; Kremblas & Foster (57) ABSTRACT

A reagent for detecting and identifying a chemical substance. The reagent is an emulsion including a cobalt salt dissolved in water which also includes at least one organic solvent that is at least partly water-miscible and also including an organic compound which serves as an ion pair color changing indicator or a pH sensitive color changing indicator, the organic compound dissolved in an organic solvent only partly miscible with water. A two product kit for detecting and identifying a chemical substance is also taught. The kit includes the aforementioned reagent and a diazonium salt, typically a diazonium salt having electron withdrawing groups on its phenyl rings. A method for detecting and identifying a chemical substance using the two product kit is also discussed. The reagent, testing kit and method may be used for detecting and identifying controlled substances.

6 Claims, 1 Drawing Sheet

FIG.1

REAGENT, A KIT, AND A METHOD FOR DETECTING AND IDENTIFYING A WIDE RANGE OF ILLICIT DRUGS

CROSS-REFERENCE TO RELATED APPLICATION

This application claims the benefit of priority from U.S. Provisional Application Ser. No. 60/935,762, filed Aug. 30, 2007, titled "A Method, a Reagent, a Field Test Kit, and A Sequence for the Detection and Identification of Chemical Substances and a Way to Stabilize Them".

FIELD OF THE INVENTION

The present invention relates to a reagent, a field kit and a method for detecting, classifying and identifying various chemical substances, particularly, illicit drugs and their groupings.

BACKGROUND OF THE INVENTION

Officials such as police officers, customs agents and the like often encounter suspect materials which are thought to contain one or more controlled substances such as illicit drugs. This encounter usually occurs under field conditions. It is often necessary to establish the nature of the suspicious substances on the spot so as to be able to detain or apprehend a suspected individual. For a number of other reasons as well, it is impractical for police or customs officers to send suspicious material to the agency's laboratories. A test of the material must be done in the field and results must usually be obtained within minutes.

Today testing for the presence or absence of illicit drugs is known as is their identification. The quickest tests known for drug detection and identification are color tests in which the response of a drug to a specific reagent is a color change. At times only the class of drug is identified; at other times the specific drug is determined. The method of testing for the presence of a drug usually requires mixing or contacting a reagent with the substance to be tested. Most if not all of the color test reagents used today are available commercially, individually or as one of a series of reagents in a multi-reagent kit.

Commonly known chemical reagents for color change testing for the presence or absence of illicit drugs include, but are not limited to, Meyer's reagent (phenolthalein/sodium hydroxide), Marquis reagent (sulfuric acid/formaldehyde), Nitric acid reagents, Cobalt thiocyanate reagent, Dille-Koppanyi reagent (cobalt acetate dehydrate/methanol/glacial acetic acid), Mandeline reagent (ammonium vanadate/sulfuric acid), Mecke's modified reagent (selenous acid/sulfuric acid), Duquenois-Levine reagent (acetaldehyde/vanillin/ethanol), Simon's reagent (sodium nitroprusside/acetaldehyde) and Zwikker's reagent (copper sulfate pentahydrate/pyridine). Classes of controlled drugs which are detectable through reagent color testing include, but are not limited to, barbiturates, amphetamines, opiates, and synthetic opiates. The National Institute of Justice (NIJ) has issued a standard through its law enforcement and correction standards and testing program called *Color Test Reagents/Kits for Preliminary Identification of Drugs of Abuse* (NIJ Standard-0604.01). This standard summarizes many drug testing procedures and reagents.

However, the performance of chemical reagent drug tests suffers from a number of drawbacks and deficiencies. From the above NIJ pamphlet and other sources it is evident that in order to test for all of the possible controlled illicit drugs, a kit containing many reagents, some of which are caustic or corrosive, is required.

Performing the tests is often potentially hazardous. For instance, many tests typically require one or more steps and the manipulation of various vials, which can be time consuming, inconvenient and dangerous. The aforementioned steps may result in mishaps and spillage of liquids which, as noted above, may be caustic or otherwise corrosive.

Currently, a few kits for testing and identifying a wide range of illicit drugs under field conditions exist. However, because the materials generally used for testing suspected materials are drug specific, a relatively large number of reagents and physical operations are still required to cover the wide range of drug possibilities when a sample is of unknown identity.

Importantly, use of the reagents and kits currently available often requires appreciable amounts of suspected material, usually an amount at least visible to the naked eye. Trace amounts of illicit materials often go undetected.

It would therefore be desirable to provide a test for field use wherein the number of reagents and tests is minimized. It would also be desirable to provide a field test kit where a minimum number of physical operations is required, reducing possible mishaps, inaccurate readings and spillage of liquids. It would also be desirable to provide field test kits where no caustic or corrosive reagents are present. Finally, it would be desirable to provide a field test kit suitable for identifying very small size samples.

SUMMARY OF THE PRESENT INVENTION

It is an object of the present invention to provide a field test kit for detecting and identifying chemical substances, particularly illicit drug materials.

It is a further object of the present invention to provide multi-drug detection reagents for use in a field test kit which allow for rapid identification of chemical substances, particularly illicit drugs. The multi-drug detection reagents are intended to provide improved color discrimination when reacting with different illicit drugs.

It is a further object of the invention to provide an emulsion which allows for rapid identification under field conditions of multiple chemical substances, particularly illicit drugs.

Another object of the invention is to provide a test kit for testing unidentified suspect material that may be located on many types of surfaces under many different field conditions.

It is yet another object of the present invention to provide a method for rapidly detecting drug residues and identifying their chemical identity. The method allows for confirming the identity of the drug or its subgroup in a minimum number of steps, specifically two steps.

There is provided in a first aspect of the present invention, a reagent for detecting and identifying a chemical substance. The reagent is an emulsion comprising a cobalt salt dissolved in water which also includes one or more organic solvents which are at least partly water-miscible; and an organic compound which serves as an ion pair color changing indicator or a pH sensitive color changing indicator, the organic compound dissolved in an organic solvent only partly miscible with water.

In one embodiment of this first aspect of the invention, the organic compound is a brominated organic compound selected from a group consisting of bromophenol red, bromocresol purple, tetrabromophenol blue, and tetrabromophenolphthalein ethyl ester.

In another embodiment of the first aspect of the invention, the organic compound is tetrabromophenolphthalein ethyl ester.

In yet another embodiment of the first aspect of the invention, the one or more organic solvents which are at least partly water-miscible is selected from a group consisting of: ethanol, methanol, propanol, isopropanol, butanol, isobutanol, glycerol, propylene glycol and dimethyl sulfoxide.

In still another embodiment of the first aspect of the present invention, the solvent for the cobalt salt comprises about 25% to about 75% water, the remainder being the one or more organic solvents which are at least partly water-miscible. In some embodiments, the one or more organic solvents which are at least partly water-miscible are one or more alcohols.

In a further embodiment of the first aspect of the invention, the solvent for the cobalt salt comprises water, isopropanol, and isobutanol in the ratio of 50%:25%:25%.

In still another embodiment of the first aspect of the invention, the organic solvent only partly miscible with water is selected from a group consisting of ethyl acetate, butyl acetate, dipropylene glycol dimethyl ether, diethyl ether, and dipropyl ether.

In yet another embodiment of the first aspect of the present invention, the organic solvent only partly miscible with water is butyl acetate.

In a second aspect of the present invention, there is provided a testing kit for detecting and identifying chemical substances. The kit includes a diazonium salt; and an emulsion. The emulsion further includes a cobalt salt dissolved in water which also includes one or more organic solvents which are at least partly water-miscible; and an organic compound which serves as an ion pair color changing indicator or a pH sensitive color changing indicator, the organic compound dissolved in an organic solvent only partly miscible with water.

In another embodiment of the second aspect of the present invention, the diazonium salt has one or more electron withdrawing substituents on its aromatic rings.

In a further embodiment of the second aspect of the invention, the one or more electron withdrawing substituents includes a nitro group.

In yet another embodiment of the second aspect of the preset invention, the diazonium salt is selected from salts of Fast Corinth V or Fast Black K.

In still another embodiment of the second aspect of the invention, the diazonium salt is dissolved immediately before use in a solvent selected from methylene chloride, methyl ethyl ketone (MEK), acetone, dimethyl sulfoxide, and N-methylpyrrolidone.

In another embodiment of the second aspect of the invention, the organic compound is a brominated organic compound selected from a group consisting of bromophenol red, bromocresol purple, tetrabromophenol blue, and tetrabromophenolphthalein ethyl ester.

In a further embodiment of the second aspect of the invention, the organic compound is tetrabromophenolphthalein ethyl ester.

In yet another embodiment of the second aspect of the present invention, the one or more organic solvents which are at least partly water-miscible is selected from a group consisting of ethanol, methanol, propanol, isopropanol, butanol, isobutanol, glycerol, propylene glycol and dimethyl sulfoxide.

In another embodiment of the second aspect of the present invention, the solvent for the cobalt salt comprises about 25% to about 75% water, the remainder being the one or more organic solvents which are at least partly water-miscible.

In yet another embodiment of the second aspect of the invention, the one or more organic solvents which are at least partly water miscible are one or more alcohols.

In yet a further embodiment of the second aspect of the invention, the solvent for the cobalt salt comprises water, isopropanol, and isobutanol in the ratio of 50%:25%:25%.

In still another embodiment of the second aspect of the present invention, the organic solvent only partly miscible with water is selected from a group consisting of: ethyl acetate, butyl acetate, dipropylene glycol dimethyl ether, diethyl ether, and dipropyl ether.

In another embodiment of the second aspect of the invention, the organic solvent only partly miscible with water is butyl acetate.

In yet another embodiment of the second aspect of the invention, the testing kit comprises two dispensers. One of the dispensers includes an ampoule containing the cobalt salt in its water-based solvent and one or more organic solvents which are at least partly water-miscible, and the other ampoule contains the organic compound which serves as an ion pair color changing indicator or a pH sensitive color changing indicator dissolved in the organic solvent only partly miscible with water. The second dispenser includes the diazonium salt and an ampoule of solvent to dissolve the diazonium salt.

In a third aspect of the present invention there is provided a multi-chemical substance detection solution comprising a nitro-diazonium salt dissolved in a solvent selected from a group of solvents consisting of: methylene chloride, methyl ethyl ketone (MEK), acetone, dimethyl sulfoxide, and N-methylpyrrolidone.

In a fourth aspect of the present invention, there is provided a method for detecting and identifying a chemical substance where the chemical substance may be one of many chemical substances. The method includes the steps of: contacting a first sample of the chemical substance to be identified with a dissolved diazonium salt, the first sample changing to a first color as a result of the contact; bringing an emulsion comprising A. a cobalt salt dissolved in water which also includes one or more organic solvents which are at least partly water-miscible and B. an organic compound which serves as an ion pair color changing indicator or a pH sensitive color changing indicator in an organic solvent only partly miscible with water into contact with a second sample of the chemical substance to be identified, the second sample changing to a second color as a result of contact with the emulsion; and comparing the first color with a first color chart and comparing the second color with a second color chart, and using the results of the comparisons together to detect and determine the identity of the chemical substance.

In another embodiment of the fourth aspect of the present invention, the method further includes the steps of: placing two ampoules in a dispenser where the first of the ampoules includes the cobalt salt dissolved in water which also includes one or more organic solvents which are at least partly water-miscible and the second of the ampoules contains the organic compound which serves as an ion pair color changing indicator or a pH sensitive color changing indicator in an organic solvent only partly miscible with water; and breaking the two ampoules immediately prior to use, and shaking the contents therefrom thereby to form the emulsion.

In yet another embodiment of the fourth aspect of the invention, the method further includes the steps of: placing an ampoule of a solvent in a dispenser which contains powder of the diazonium salt; and breaking the ampoule immediately prior to use, so that the solvent dissolves the diazonium salt.

In still another embodiment of the fourth aspect of the invention, the method further includes the step of wiping a surface suspected of containing a chemical substance with collection paper and in the steps of contacting and bringing, contacting is done to that part of the collection paper that has touched the wiped surface.

In yet another embodiment of the fourth aspect of the invention, the contacting in the steps of containing and bringing may be effected by any one of the following methods: spraying the dissolved reagents using an aerosol spray; hand pumping the dissolved reagents; or using a liquid dropper to deliver droplets of the dissolved reagents to the collection paper.

In an embodiment of the fourth aspect of the invention, the diazonium salt has one or more electron withdrawing substituents on its aromatic rings. In some instances, the one or more electron withdrawing substituents includes at least one or more nitro groups.

In another embodiment of the fourth aspect of the present invention, the organic compound serving as the color changing indicator is selected from a group consisting of: bromophenol red, bromocresol purple, tetrabromophenol blue, and tetrabromophenolphthalein ethyl ester.

In still another embodiment of the fourth aspect of the invention, the organic compound serving as the color changing indicator is tetrabromophenolphthalein ethyl ester.

In still another aspect of the present invention, the aforementioned reagent is used for detecting and identifying illicit drugs.

In still another aspect of the present invention, the aforementioned testing kit is used for detecting and identifying illicit drugs.

In still another aspect of the present invention, the aforementioned multi-chemical substance detection solution is used for detecting and identifying illicit drugs.

In still another aspect of the present invention, the aforementioned method is used for detecting and identifying illicit drugs.

In still another aspect of the present invention, a diazonium salt having one or more electron withdrawing group on a phenyl ring is used as a multi-illicit drug detector.

BRIEF DESCRIPTION OF THE DRAWING

The invention is herein described, by way of example only, with reference to the accompanying drawing. With specific reference now to the drawing in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in greater detail than is necessary for a fundamental understanding of the invention. The description taken with the drawing makes apparent to those skilled in the art how the invention may be embodied in practice.

DESCRIPTION OF PREFERRED EMBODIMENTS

The present invention teaches a simple, quick, two step detection and identification scheme for illicit drugs. The invention also teaches a field test kit with two product reagents one for each step of the detection and identification process. The kit is readily usable under field conditions by police departments, customs services and other like institutions. One of the product reagents is a novel emulsion which allows for identification of a large variety of drugs in the second step of the method.

The main difference between the test kit of the present invention and competitor kits is its ability to detect and identify. It has the ability to locate drug residues on surfaces even when the drug is not visible. The sensitivity of the two step test kit of the present invention is such that it is capable of detecting illicit drugs in amounts of less than one microgram. Competitor kits usually can only identify drugs when larger quantities of material are available, trace quantities often going undetected.

In the discussion herein, the term "multi-drug detection reagent" means any color producing reagent that reacts with at least two different drugs, producing noticeably different colors with each.

The present preferred embodiments will be discussed in the context of detecting and identifying illicit drugs. It should be readily understood by one skilled in the art that with relatively small modifications the kit, the reagents, and the method discussed herein may be appropriately modified for use with other chemical substances such as environmental contaminants, and the like.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

The Kit

The present invention provides for a two product test kit for detecting and identifying illicit drugs. The kit is intended to be used in the two step "filtering" method described below. The kit contains a first product, herein referred to as the "diazonium product" or the "D4D product", and a second product herein denoted as the "cobalt/organobromo product" or as the "C&H product".

Diazonium Product (D4D Product)

The first product, the diazonium product, contains a diazonium salt, typically a diazonium salt that includes at least one electron withdrawing group such as $-NO_2$ (nitro) and $-SO_3H$ (sulfonic) on its aromatic ring(s). Use of electron withdrawing groups such as $-NO_2$ makes diazonium salt dyes generally more reactive and allows them to react with more compounds producing different colors with different structured compounds.

For long term stability the diazonium salt is packaged separately from its solvent, herein the "D4D solvent", typically, but without intending to limit the invention, methyl ethyl ketone (MEK) or, even more preferably, methylene chloride. It is to be understood that other solvents may also be used, solvents such as acetone, dimethyl sulfoxide (DMSO), and N-methylpyrrolidone.

Typical diazonium salts that can be used for the D4D product are salts of Fast Corinth V (4',5-dimethyl-2'-nitro-3-methoxyazo-benzene) or Fast Black K (2,5-dimethoxy-4-[(4-nitrophenyl)azo]benzene). These are to be deemed exemplary salts only, and there is no intent at limiting the invention to these salts.

The diazonium salt may be packaged as a powder in a container/dispenser, typically a flexible plastic tube. Alternatively, the diazonium salt powder may be diluted and packaged with either glass microspheres or a porous polyethylene material on which the diazonium salt powder is physically absorbed.

A sealed breakable ampoule containing the D4D solvent, typically methyl ethyl ketone (MEK) or more preferably methylene chloride, is placed within the container/dispenser, the flexible plastic tube. Immediately prior to use, the ampoule is broken and the solvent is released. The tube is shaken and the diazonium salt is dissolved in the solvent. This mode of packaging is required since the dissolved diazonium salt is unstable over time.

Typically, concentrations of the dissolved diazonium salt range from about 0.01% to about 1% by weight of the solution. Even more preferably they range from about 0.05% to about 0.2% by weight of the solution.

Cobalt/Organobromo Product (C&H Product)

The second product, the cobalt/organobromo product, also referred to herein as the C&H product, includes two reagent solutions.

The first reagent contains a cobalt salt, typically but without intending to limit the invention, cobalt thiocyanate. The cobalt salt is dissolved in water, typically also containing one or more organic solvents which are at least partly water miscible. These at least partly water miscible organic solvents include, but are not necessarily limited to, glycerol, propylene glycol, isopropyl alcohol, isobutyl alcohol, ethyl alcohol, methyl alcohol. Dimethyl sulfoxide may also be used.

The water:organic solvent(s) mixtures which are used to dissolve the cobalt thiocyanate is typically in the range of from about 3:1 to about 1:3 v/v and more preferably from 3:2 to about 2:3 v/v.

A preferred formulation of the cobalt thiocyanate solution used in the kit of the present invention includes cobalt thiocyanante in an amount from about 0.1% to about 2%, water in an amount from about 90% to about 10%, and the at least one organic solvent in an amount from about 10% to about 90% by weight of the solution.

The cobalt salt dissolved in the water/organic solvent(s) mixtures such as those described above is stored in a first breakable glass ampoule until it is to be used.

The second reagent solution of the C&H product contains at least one pH sensitive color changing reagent and/or at least one ion pairing, color changing reagent. Typically, this color changing reagent is a brominated organic compound, also typically but without intending to limit the invention, 3',3", 5',5'-tetrabromophenolphthalein ethyl ester, herein designated for short as tetrabromophenolphthalein ethyl ester.

Organobromo compounds which may be used instead of tetrabromophenolphthalein ethyl ester in the organobromo reagent of the C&H product include, but without intending to limit the invention, bromophenol red, bromocresol purple, and tetrabromophenol blue.

The brominated compound is dissolved in an organic solvent only partly miscible with water. Typically, but without intending to limit the invention, this organic solvent may be chosen from the following group of solvents: ethyl acetate, butyl acetate, dipropylene glycol dimethyl ether, diethyl ether, and dipropyl ether. The dissolved brominated organic solution is stored in a second breakable glass ampoule until it is required for use.

The organobromo color changing reagent constitutes from about 0.01% to about 0.2% by weight of its solution with an organic solvent only partly miscible with water.

The first and second glass ampoules of the C&H product are kept in a single container/dispenser, typically a second flexible plastic tube, until immediately before use. The ampoules are broken and the cobalt salt solution and the organobromo compound solution are mixed immediately before use and the tube shaken to form an emulsion within the dispenser. Because the emulsion is formed immediately before use, it does not have sufficient time to separate out into two distinct layers. Keeping the cobalt and organic layers in separate layers which are then emulsified, effectively increases distinct color formation for different drugs. This allows for a wider range of drugs to be detected and identified. It was found that the time for the solutions of the emulsion to separate is an important parameter that influences the drug identification reactions.

The ratio between the cobalt reagent to the organobromo reagent used to form the emulsion of the C&H product is from about from 1.4 to about 1:1 v/v.

An emulsifier may optionally be added to one of the solvents in one of the reagent solutions of the C&H product before placing the reagent into its breakable ampoule. The emulsifier prolongs the stability of the emulsion when it is later formed. The emulsifier may be chosen from many different emulsifiers readily available commercially, such as the Emcol group of emulsifiers distributed by Witco Chemicals.

The testing kit therefore contains a pair of flexible plastic tubes, i.e. containers/dispensers; one tube contains the diazonium product while the second tube contains the cobalt/organobromo product.

Figure 1:
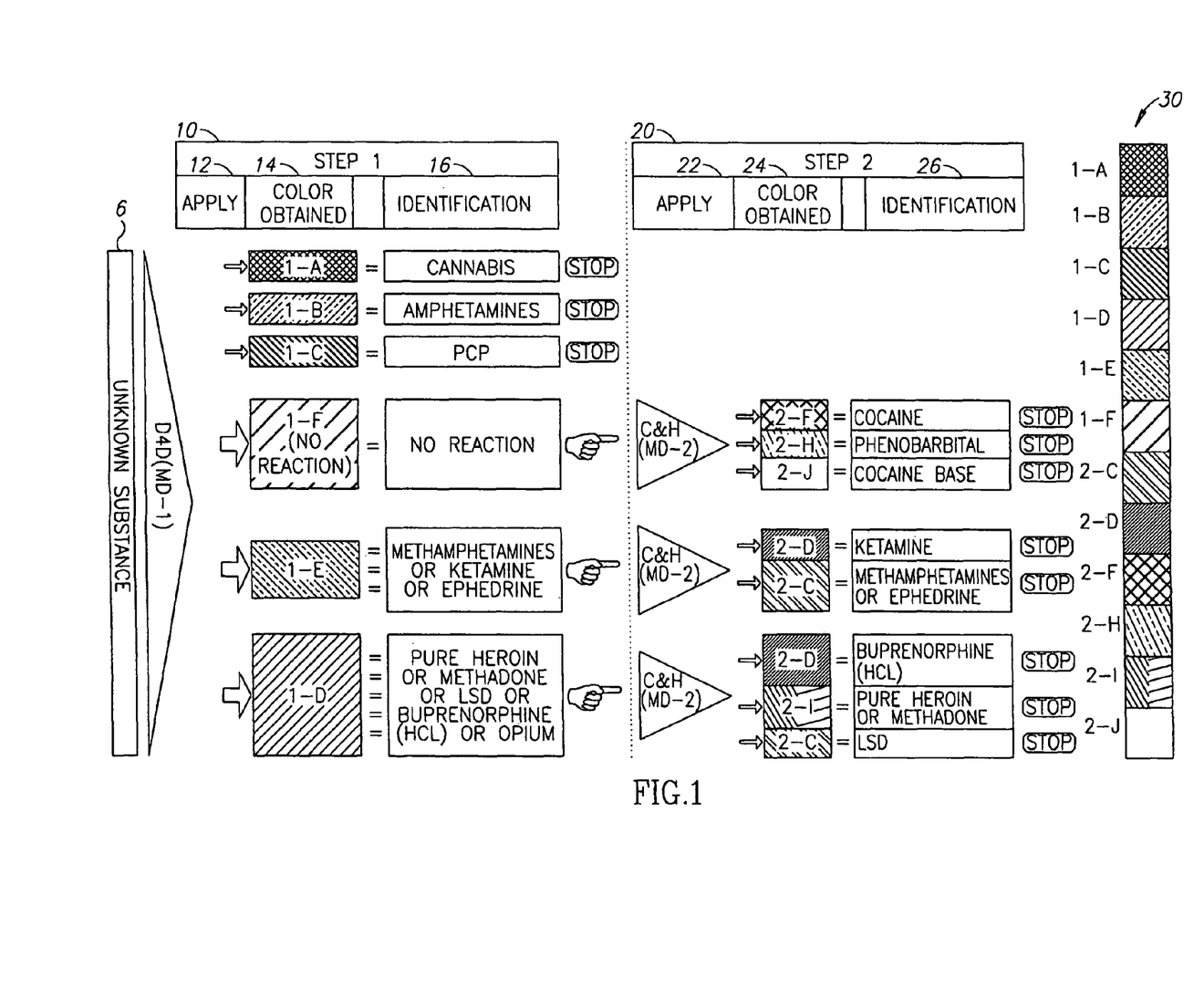
FIG. 1 is a flowchart of the two stage detection and identification method provided by the present invention.

This two product test kit containing the D4D and C&H products allows for a simple rapid determination of a wide range of illicit drugs as shown in FIG. 1 to which reference is now made. FIG. 1 is a flowchart of the detection process when using the test kit. FIG. 1 shows that by first applying 12 the D4D product to a first sample of a suspect unknown substance 6 in step 1 (step 1 being denoted by number 10) and then applying 22 the C&H product to a second sample of unknown substance 6 in step 2 (step 2 being denoted by number 20), at least eleven different drugs or drug groups can be identified. It should be noted that as shown in Table II below, many more than eleven different drugs can be detected and identified by applying the two product test kit in the illustrated two step process. Eleven drugs are shown here in an effort to keep FIG. 1 as uncluttered as possible. Note that in FIG. 1, the D4D product is also referred to as the MD-1 product and the C&H product is also referred to as the MD-2 product.

FIG. 1 shows that after applying 12 the D4D product of the test kit to the unknown substance, various colors are obtained. These colors are indicated as 1-A through 1-F in the rectangles located below "color obtained" heading 14. The actual colors obtained are listed in Table I below. By comparing the color obtained 14 to a color chart 30, the drug or drug group of unknown substance 6 is identified as shown in the rectangles below "identification" heading 16.

FIG. 1 also shows that in step 2 (denoted by number 20) the C&H product is applied 22 to a second sample of unknown substance 6. After applying 22 the C&H product to the second sample of unknown substance 6, a color change occurs as indicated in the rectangles below "color obtained" heading 24. Various colors are obtained as indicated in the rectangles marked 2-D through 2-J. The actual colors obtained are listed in Table I below. The color obtained is compared to a color chart 30 and the drug or drug group is identified as indicated in the rectangles below the "identification" heading 26.

It should be noted that the multiple triangles under step of applying 22, showing the application of the C&H product, in effect refer only to a single application of the C&H product to the second sample. Multiple triangles are shown solely for ease of presentation and to better indicate the color discrimination between the various identifiable drugs shown below "identification" heading 26.

As noted above, Table I below shows the colors resulting from reacting the D4D and C&H products with various drugs as indicated by the number-letter combinations in the "color obtained" rectangles of FIG. 1

TABLE I

| Letter and number | Color |
| --- | --- |
| 1-A | Red |
| 1-B | Yellow |
| 1-C | Purple |
| 1-D | Purple-brown |
| 1-E | Orange |
| 1-F | Beige |
| 2-C | Purple |
| 2-D | Greenish |
| 2-F | Turquoise-greenish |
| 2-H | Purple |
| 2-I | Purple/violet + light blue |
| 2-J | Sky blue |

In some embodiments, the kit may contain duplicates of the D4D and C&H products to allow for repeating the test if required.

In some embodiments of the test kit, the kit may also contain known prior art commercially available single product tests for testing individual illicit drugs. These can be used to confirm the identification obtained with the two step test kit of the present invention discussed above.

In other embodiments of the kit, the kit may also include a set of collection paper dispensers. One dispenser may contain a filter paper laminated with polyethylene while another may contain a polyethylene laminated filter paper impregnated with different chemicals to allow for changing the pH.

The recommended temperature for use of the kit is between 0-40° C.

The kit contains neither poisonous nor carcinogenic reagents and is environmentally friendly.

Personnel employing the kit do not require special training since use of the kit is simple, efficient and easy. Moreover, use of the kit does not require protective means.

Preparation of the Reagents

The following are illustrative examples for preparing the D4D and C&H products of the kit described herein above and used for the experiments described herein below.

Preparation of the Diazonium Salt

The active material in the D4D product of the kit is a Fast Corinth V salt that is stabilized by a method described in U.S. Pat. No. 4,771,005, herein incorporated by reference.

The stabilization of Fast Corinth V salt is carried out as follows.

50 g of Fast Corinth V zinc chloride double salt (Sigma: catalogue no 227366) is dissolved in 2.5 liters of distilled water. Six teaspoons of ashless powder (Whatman: catalogue no. 1700-025) is added to the solution. The solution is vacuum filtered through a double layer of filter paper. The solution obtained has a clear reddish-brown hue without sediment or floating particles. In the event that such particles are present, the solution is filtered again.

A solution of sodium tetrafluoroborate is prepared by dissolving 50 g of sodium tetrafluoroborate in 300 ml of distilled water. The $NaBF_4$ solution is added to the filtered Fast Corinth V (FCV) salt solution while mixing. When adding the sodium tetrafluoroborate solution to the FCV solution, the solution turns a strong non-transparent yellow hue. The solutions are mixed for 20 minutes and then they are passed through a vacuum filter using a double layer of filter paper (Whatman).

The resulting solid is washed with a little distilled water and then dried overnight under continuous vacuum in an oven at 50° C.

A thin cake of Fast Corinth V $BF_4$ (FCVB) is obtained on the filter paper. Since the FCVB dust is sensitive to both light and humidity, the cake is crumbled and stored in a dry dark bottle covered with aluminum foil in a dark cool place. For long term storage, the Fast Corinth V BF4 salt should be stored in a refrigerator.

It should be noted that as in U.S. Pat. No. 4,771,005, the Fast Corinth V compound may also be stabilized by forming a perchlorate or picrate salt rather than the tetrafluoroborate salt.

Preparation of the D4D Product

The D4D product is comprised of Fast Corinth V $BF_4$ (FCVB) dust in the amount of about 0.00068 g and a glass ampoule containing about 0.5 ml of methylene chloride or alternatively methyl ethyl ketone (MEK). The FCVB dust and the ampoule are separately inserted unto a common container/dispenser, typically a flexible plastic tube, and they are kept apart from each other until the product is ready for use.

It has been found that the diazonium salts used are stabilized when dissolved in organic solvents vis-a-vis when dissolved in water or water/organic solvent mixtures. A solvent such as methylene chloride, and less preferably methyl ethyl ketone (MEK), is therefore used. Additionally, working in an organic solvent allows for greater color contrast with the background when the D4D product reacts with an illicit drug.

There are three methods of inserting the Fast Corinth V BF4 dust into the flexible plastic tube i.e. the dispenser.

A. Loading Fast Corinth V $BF_4$ (FCVB) in the Desired Amount to Form a Batch in Methylene Chloride.

A solution containing about 0.0006 g of FCVB in about 0.5 ml of solvent is decanted into a flexible plastic tube. The tube is placed into an oven for three hours at 50° C. and heated until the dust is dry. A glass ampoule containing 0.5 ml of methylene chloride or MEK is then inserted into the plastic tube containing the dry dust.

B. Mix the Fast Corinth V BF4 Dust in a Known Concentration with Glass Microspheres (Sigma: Catalogue No 440345)

A mixture is formed by adding about 0.0006 g of Fast Corinth V BF4 in 0.5 ml of methylene chloride to about 50 mg of glass microspheres. The solvent is evaporated while continuously stirring until absolutely dry FCVB dust is obtained. The dust and microspheres are placed in a glass ampoule and then the ampoule is inserted into a flexible plastic tube. A second ampoule containing 0.5 ml methylene chloride or MEK is then inserted into the tube. Immediately before using the D4D product, both ampoules are broken and the tube is shaken to dissolve the FCVB dust in the organic solvent.

In order to fill ampoules with the small amounts of FCVB required in an industrial setting, there is a need to increase the total amount of material filling the ampoules without increasing the actual amount of the active ingredient, FCVB. This is the purpose of using the glass microspheres. The glass microspheres are absolutely inert and therefore can be used to complete the required amount of material for filling the ampoule. Tests indicated that the glass microspheres had no affect on the different test reactions occurring between the diazonium salt and the various illicit drugs.

C. Absorption of the Active Material Fast Corinth V BF4 in Porex.

Porex is a material made from porous polyethylene (Porex: catalogue no. XM-0266). The porous polyethylene used as the substrate for absorbing FCVB had a size of 3.05×1.75 mm. It is possible to put these directly into a flexible plastic tube/dispenser instead of into a glass ampoule. The porous polyethylene absorbs a small amount of Fast Corinth V $BF_4$ salt, thereby solving the problem of industrially filling ampoules with the required amount of material without increasing the amount of the active ingredient, FCVB.

The porous polyethylene particles are placed into a solution of about 0.0006 g of Fast Corinth V $BF_4$ salt dissolved in about 0.5 ml methylene chloride. Each particle absorbs the FCVB solution. The methylene chloride is evaporated in an evaporator in order to obtain polyethylene particles that have substantially equal concentrations and quantities of FCVB dust in them. The ampoule containing the Porex particles having FCVB dust absorb on them is inserted into a flexible plastic tube. A second breakable glass ampoule containing 0.5 ml methylene chloride or MEK is then inserted into the flexible plastic tube. Immediately before use, both ampoules are broken and the tube is shaken to dissolve the FCVB in the solvent.

Preparation of the C&H Product

The C&H product is an emulsion formed from two solution reagents:

A. an organic compound which serves as an ion pair color changing indicator or a pH sensitive color changing indicator, the organic compound being dissolved in an organic solvent only partly miscible with water. Typically, but without limiting the invention, the solvent is butyl acetate; and B. an aqueous solution containing a cobalt salt, the aqueous solution also containing at least one organic solvent which is at least partly water miscible. The at least one organic solvent may be, but without limiting the invention, isobutanol and/or isopropanol.

The C&H product is comprised of reagent solutions A and B as described above with each of the solutions kept in separate glass ampoules to stabilize the product and lengthen its shelf life. Immediately prior to use, the ampoules are broken, and their contents are shaken together to obtain the above described emulsion.

First Ampoule

The active agreement in the solution found in this ampoule is typically tetrabromophenolphthalein ethyl ester (Sigma: catalogue no 86778).

The tetrabromophenolphthalein ethyl ester >0.05% is dissolved in 100 ml butyl acetate. The total volume of solution placed in a breakable first glass ampoule is 0.6 ml.

Second Ampoule

The cobalt reagent is prepared as follows.

About 0.0077 g of cobalt thiocyanate is dissolved in 0.3 ml of water. The solution that is obtained is filtered. After filtering, a clear pink solution without floating particles is obtained. Isobutyl alcohol (IBA) in the amount of about 0.15 ml and isopropyl alcohol (IPA) in the amount of about 0.15 ml are added to the solution.

The solvent mixture used is typically a water:IBA:IPA mixture in the ratio 2:1:1 v/v. A wide range in the ratios of the solvents may be used. Water may be as little as 25% v/v and as much as 75% v/v of the solvent mixture with the remainder an organic solvent, or solvents, chosen from among those previously discussed.

The water, isobutyl alcohol (IBA), isopropyl alcohol (IPA) solution containing the cobalt salt is placed in a second breakable glass ampoule. The total volume of the solution placed in the second ampoule is 0.4 ml.

When the first and second ampoules are broken and their contents mixed immediately prior to use, an emulsion is produced. This allows for simultaneous dispensing of both of the above described reagent solutions, A and B, of the C&H product.

Forming an emulsion is an important part of the success of the present invention. If the cobalt salt and the organic compound which serves as an ion pair color changing indicator and/or a pH sensitive color changing indicator were mixed and dissolved in a single phase, no reaction, or at most a barely noticeable reaction, would occur with many illicit drugs. The use of an emulsion allows for the reactions of the individual reagents in each of the emulsion's phases to occur simultaneously, but separately. The different reagents in the emulsion's two layers do not interfere with, or cancel out, each other.

If the reagents in the two emulsion layers were applied sequentially, the components would not produce the desired color discrimination between different drugs. If applied sequentially, the first reagent would react with all of the illicit drug residues since these are usually present in amounts smaller than that of the first reagent. As a result, the second reagent would not react at all.

It will be evident to those skilled in the art that the invention is not limited to the details of the foregoing illustrative examples for preparing the reagents/products of the present invention. The invention may be embodied in other specific forms without departing from the essential attributes thereof, and it is therefore desired that the detailed examples above be considered in all respects as illustrative and non-restrictive.

Method of Use

The method of testing for illicit drugs using the kit described herein above is a two step "filtering" process suitable for use under field conditions. FIG. 1, to which reference has already been made, indicates the illicit drug/narcotic two-step screening process taught by the present invention. The flowchart shows the division of the drugs into groups. When an unknown material which is suspected as being an illicit drug is tested, the method of the present invention identifies and classifies it in a quick easy manner using only two reagent products.

In the first step, the D4D product described herein above divides the drugs into groups, while explicitly identifying some of the drugs. As can be seen in FIG. 1, the drugs shown in color/drug groups 1A, 1B and 1C have been identified. In the second step the C&H product extends the results obtained in the first step and detects additional specific illicit drugs. D4D identifies different groups, amphetamines, hashish, phencyclidine (PCP), heroin and its family and methamphetamines and its family while C&H identifies cocaine, crack, phenobarbitol, methamphetamines ketamines, ephedrine, heroin, methadone, LSD and buprenorphine.

It is to be understood that while the method for collection, detection and identification of an illicit drug according to the present invention, can be applied in its entirety, in some embodiments of the invention a single step of the method can be used alone, sometimes in conjunction with other known reagents, to identify specific individual illicit drugs.

When a material is located which is suspected of being a drug of unknown nature, the kit provided by the present invention allows for an unequivocal determination in just two readings. By examining the color produced on one sample of the suspect material using the D4D product and the color produced on a second sample by the C&H product, the suspect material is identified. Using competitive kits for the same broad range of possible illicit drugs would require testing with at least 10 specific reagents.

The method of use of the testing kit provided by the present invention includes the steps of:

A. collecting two samples of the suspect material;
B. contacting the D4D product to one of the samples;
C. contacting the C&H product to the other sample; and
D. comparing the colors of both samples to charts and the comparisons, taken in conjunction with each other, are then used to identify the suspect material.

As shown in Table II below at least 20 illicit drugs may be identified using this method.

Method of Collecting Samples

A surface containing a suspect material is wiped with a piece of collection paper. The collection paper collects residues that may or may not be visible to the eye.

The collection paper that may be provided with the two step testing kit of the present invention has two layers. The backside is comprised of a layer of polyethylene. This prevents undesired contact between the investigator with the suspect material or the surface being wiped. On its front side, the collection paper is protected by a layer of silicon. This also prevents contamination of the collection paper.

The method of collecting samples used with competitor kits requires that each test contain a certain relatively large quantity of the suspect material, typically a few milligrams (mg). Generally, only a quantity that is visible can be collected and tested using competitor kits. The kit provided by the present invention is sensitive to samples of less than a microgram.

The chance of collecting residues of suspect materials from a surface decreases with the number of wipings. Therefore, a kit that requires only two wipings, i.e. two samples, such as the kit of the present invention, increases the chances of identification over a kit that requires three or more wipings, i.e. three or more samples, as do prior art kits.

First Step—Applying the D4D Product:

After taking a piece of collection paper and wiping the suspect surface or touching the paper to the suspect material, the ampoule containing the solvent for the diazonium salt found in the first flexible plastic tube/dispenser is broken. The tube is shaken well for 10 seconds in order to dissolve the diazonium salt powder in the tube/dispenser with the methylene chloride or MEK solvent.

Using a liquid dropper, drops, typically but without limiting the invention, between one to five drops, of the dissolved diazonium salt are placed on the paper at the point the paper touched the suspect material. The resulting color is then compared to a color ruler indicating the various colors produced by different drugs when they come into contact with the D4D product.

The D4D product identifies five different groups of drugs with a single wiping by producing five different colors, each color being indicative of a different group of illicit drugs. There is also the possibility of testing a drug group which does not produce a color change.

In addition to applying the D4D product by means of a liquid dropper, the reagent may be applied onto the collection paper, by any of several other dispensing means. Without limiting the invention these include, spraying the D4D product using an aerosol spray, or applying the D4D solution with a hand pump, or by dripping the contents of the tube/dispenser directly onto the collection paper at its point of contact with the suspect material.

Second Step—Applying the C&H Product

In order to know which of the possible drugs is the actual drug present, the C&H product in the kit is used. A second sample of the suspect material is collected by using another piece of collection paper to wipe or touch the suspect material or the surface on which the suspect material is present.

The C&H product's two ampoules found in the second plastic tube/dispenser of the kit are broken and their contents shaken for ten seconds. An emulsion is formed. Several drops of the emulsion are placed on that portion of the collection paper which touched the suspect material. Typically, the drops are delivered using a liquid dropper. The color resulting from the C&H product reacting with the suspect material is compared to a table of colors and the identity of the illicit drug is determined.

In some embodiments of the invention, the two reagents of the C&H product with their respective solvents may be placed in a pressurized aerosol container. The pressure may be produced by an evaporating liquefied material or a compressed gas. According to the mixture ratio, valves, with or without vapor tap, can be used. The C&H product is then sprayed onto the collection paper at its point of contact with the suspect material. A method for providing aerosol containers for applying drug detection chemicals has been described in U.S. Pat. No. 4,812,413, herein incorporated by reference.

According to yet other embodiments of the invention, a hand pump may be used to deliver or contact the emulsion with the suspect material. Alternatively, the C&H emulsion product may be dripped directly from the plastic tube/dispenser onto the point of contact of the collection paper with the suspect material.

As noted above, the developed color of the first sample is observed and checked against a color chart. Then the developed color of the second sample is observed and compared to a color chart. The comparisons used in conjunction with each other allow for identification of the material as is readily seen from FIG. 1.

By performing the above sequence of tests, the specificity of the field kit and its individual reagents/products can be increased. The first multi-drug detection product divides a group of illicit drugs into 6 (5 and a negative) subgroups. Some of the illicit drugs in a single subgroup react with the second multi-drug detection product providing color discrimination between the illicit drugs that was not achievable with the first product alone. Similarly, if the second multi-drug detection product reacts the same with a group of different illicit drugs, it is possible that the first multi-drug detection product when used to test the same group of drugs produces different color changes for each drug. For example, amphetamine sulfate and methamphetamine sulfate react similarly with the second product, the C&H product, producing the same color. However, they produce different colors when reacting with the first product, the D4D product. Therefore, the two products used in concert increase the specificity of the kit and its reagents/products.

As can be seen from Table II below, the two step kit using the D4D product and the C&H emulsion product allows for differentiation between a large number of common illicit drugs.

Experiments

After preparing formulations of the D4D and C&H products in the manner outlined above in the reagent section, a large number of illicit drugs in known quantities and concentrations were tested. These were tested to see if the two step kit reacts with the illicit materials and provides a sufficiently broad range of discriminating colors. The results are summarized in Table II below.

As shown in Table II, a large number of commonly available materials were also tested. These included innocuous licit materials and over-the-counter legal drugs. The test was carried out by two people to confirm the identification(s) obtained.

TABLE II

| | D4D | | C&H | |
|---|---|---|---|---|
| Drug | reaction time | Color (NR—No Reaction) | reaction time | Color (NR—No Reaction) |
| Marijuana/hashish | immediately | Red | | NR |
| cocaine | | NR | immediately | turquoise |
| crack | | NR | immediately | blue |
| PCP | 90 sec | Purple | immediately | blue + violet |
| Methadone | 45 sec | dark brown | immediately | blue + violet |
| Pure Heroin | 45 sec | dark brown | | violet |
| Buprenorphine | 45 sec | dark brown | 25 sec | greenish + turquoise |
| Morphine | | NR | | NR |
| Codeine | | NR | immediately | purple |
| Oxycodone | | NR | | NR |
| Opium | 45 sec | dark brown | | NR |
| LSD | 45 sec | dark brown | immediately | bright blue |
| Diphenhydramine | | NR | immediately | violet + blue |
| Quinine | | NR | immediately | violet + blue |
| Amphetamine | 45 sec | Yellow | | NR |
| Barbiturate | | NR | immediately | dark blue + violet |
| Methamphetamine | 45 sec | Orange | immediately | dark blue + purple |
| Ephedrine-base | 45 sec | Orange | immediately | violet |
| Ephedrine-HCL | 45 sec | Orange | immediately | violet |
| Psedoephedrine | 45 sec | Orange | immediately | purple/violet + light blue |
| MDMA | 45 sec | Orange | immediately | purple blue |
| Ketamine | 45 sec | Orange | 20 sec | light turquoise |
| Thebaine | | NR | | purple blue |
| Coffee | | NR | | NR |
| Sugar | | NR | | NR |
| soup powder | | NR | | NR |
| baking powder | | NR | | NR |
| washing powder | | NR | | NR |
| Salt | | NR | | NR |
| Acamol | | NR | | NR |
| Aspirin | | NR | | NR |
| Tea | | NR | | NR |
| Flake soap | | NR | | NR |
| Flour | | NR | | NR |

As noted previously, the description herein relates to a kit, reagents, and a method for illicit drug detection and identification. It should be appreciated that the invention may be effective for collecting, detecting and identifying other materials, such as environmental contaminants and the like. These would require slight but not insurmountable changes to the reagents, changes that should be readily attainable by persons skilled in the art.

All of the abovementioned parameters and quantities are given by way of example and illustration only, and may be changed in accordance with the different requirements of the various embodiments of the present invention. Thus, the abovementioned parameters and quantities should not be construed as limiting the scope of the present invention in any way. A person skilled in the art can carry out the invention in a great variety of ways, employing more than one technique selected from those described above, or otherwise generally known, all without exceeding the scope of the invention. In addition, it is to be appreciated that the reagents, dispensers, collection media, aerosols, and other elements, described hereinabove may be constructed in different shapes and sizes from those exemplified in the preceding description.

It is to be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention. Therefore, it will be appreciated by persons skilled in the art that the present invention is not limited by what has been particularly shown and described herein above. Rather, the scope of the invention is defined by the claims that follow.

What is claimed is:

1. A reagent for detecting and identifying a chemical substance, said reagent being an emulsion comprising:
a cobalt salt dissolved in water which also includes at least one organic solvent which is at least partly water-miscible; and
an organic compound which serves as an ion pair color changing indicator or a pH sensitive color changing indicator, said organic compound dissolved in an organic solvent only partly miscible with water.

2. A reagent for detecting and identifying a chemical substance according to claim 1 wherein said organic compound is a brominated organic compound selected from a group consisting of: bromophenol red, bromocresol purple, tetrabromophenol blue, and tetrabromophenolphthalein ethyl ester.

3. A reagent in detecting and identifying a chemical substance according to claim 1 wherein said at least one organic solvent which is at least partly water-miscible is selected from a group consisting of: ethanol, methanol, propanol, isopropanol, butanol, isobutanol, glycerol, propylene glycol and dimethyl sulfoxide.

4. A reagent in detecting and identifying a chemical substance according to claim 1 wherein said solvent for the cobalt salt comprises about 25% to about 75% water, the remainder of the solvent being said at least one organic solvent which is at least partly water-miscible.

5. A reagent in detecting and identifying a chemical substance according to claim 1 wherein said solvent for the cobalt salt comprises water, isopropanol, and isobutanol in the ratio of 50%:25%:25%.

6. A reagent for detecting and identifying a chemical substance according to claim 1 wherein said organic solvent only partly miscible with water is selected from a group consisting of ethyl acetate, butyl acetate, dipropylene glycol dimethyl ether, diethyl ether, and dipropyl ether.

* * * * *